(12) United States Patent
Barnhart et al.

(10) Patent No.: US 7,943,324 B2
(45) Date of Patent: May 17, 2011

(54) ENDOMETRIOSIS MARKERS

(75) Inventors: Kurt T. Barnhart, Bryn Mawr, PA (US);
Beata Seeber, Ardmore, PA (US);
George L. Gerton, Bryn Mawr, PA (US); Mary D. Sammel, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/643,956

(22) Filed: Dec. 22, 2006

(65) Prior Publication Data
US 2007/0264270 A1 Nov. 15, 2007

(51) Int. Cl.
*G01N 33/53* (2006.01)
(52) U.S. Cl. .................... 435/7.1; 435/7.2; 436/518
(58) Field of Classification Search .................. None
See application file for complete search history.

(56) References Cited

U.S. PATENT DOCUMENTS

| | | | | |
|---|---|---|---|---|
| 6,777,182 B2 * | 8/2004 | Baban et al. | ...................... | 435/6 |
| 2003/0186300 A1 | 10/2003 | Akoum | | |

OTHER PUBLICATIONS

Matarese et al. (J. Clin. Endocrin. Metabolism 2000 vol. 85, p. 2483-2487).*
Katz (Fertility & Sterility 2002 vol. 78, p. 69-76).*
Patton et al. (Fertility & Sterility 1986 vol. 45, p. 770-773).*
Vlahou A et al. "Diagnosis of Ovarian Cancer Using Decision Tree Classification of Mass Spectral Data" J Biomed Biotechnol. 2003; 2003(5): 308-314.
Barnhart, K. et al. 1994. Prompt diagnosis of ectopic pregnancy in an emergency department setting. Obstet. Gynecol. 84: 1010-1015. 8.
Barnhart, K.T. et al. 2003. The medical management of ectopic pregnancy: a metaanalysis comparing "single dose" and "multidose" regimens. Obstet Gynecol. 101: 778-784.
Barnhart, K.T. et al. 2002. Presumed diagnosis of ectopic pregnancy. Obstet. Gynecol. 100: 505-510.
Bjartling, C, S. Osser & K. Persson. 2000. The frequency of salpingitis and ectopic pregnancy as epidemiologic markers of Chlamydia trachomatis. Acta Obstet. Gynecol. Scand. 79: 123-128.

Bouyer, J. et al. 2003. Risk factors for ectopic pregnancy: a comprehensive analysis based on a large case-control, population-based study in France. Am. J. Epidemiol. 157:185-194.
Bronson, R. & M. Cunnane. 1975. Transfer of uterine implantation blastocysts to the oviduct in mice. Fertil. Steril. 26: 455-459.
Felemban, A., A. Sammour & T. Tulandi. 2002. Serum vascular endothelial growth factor as a possible marker for early ectopic pregnancy. Hum. Reprod. 17: 490-492.
Gracia, C.R. & K.T. Barnhart. 2001. Diagnosing ectopic pregnancy: decision analysis comparing six strategies. Obstet. Gynecol. 97: 464-470.
Hunter, R.H. 2002. Tubal ectopic pregnancy: a patko-physiological explanation involving endometriosis. Hum. Reprod. 17:1688-1691.
Johnson, M.R. et al. 1993. Interactions between the embryo and corpus luteum. Hum. Reprod. 8: 1496-1501.
Lemus, J.F. 2000. Ectopic pregnancy: an update. Curr. Opin. Obstet Gynecol. 12: 369-375.
Mol, B.W., F. van Der Veen St. P.M. Bossuyt. 1999. Implementation of probabilistic decision rules improves the predictive values of algorithms in the diagnostic management of ectopic pregnancy. Hum. Reprod. 14: 2855-2862.
O'Day-Bowman, MJ3. et al. 1995. A human oviduct-specific glycoprotein: synthesis, secretion, and localization during the menstrual cycle. Microsc. Res. Tech. 32: 57-69.
Sauer. M.V. et al. 1989. Predictive value of a single serum pregnancy associated plasma protein-A or progesterone in the diagnosis of abnormal pregnancy. Hum. Reprod. 4:331-334.
Seppala, M. & M. Purhonen. 1987. The use of hCG and other pregnancy proteins in the diagnosis of ectopic pregnancy. Clin. Obstet. Gynecol. 30: 148-154.
Sinosich, M.J. et al. 1985. Circulating and tissue concentrations of pregnancy-associated plasma protein-A (PAPP-A) in tubal ectopic gestation. Clin. Reprod. Fertil. 3: 311-317.
Tay, J.I., J. Moore & JJ. Walker. 2000. Ectopic pregnancy. Brit. Med. J. 320:916-919.
Akoum, et al 1996 "Increased monocyte chemotactic protein-1 level and activity in the peripheral blood of women with endometriosis" Am Journal Obstet Gynecol 1620-1625.

* cited by examiner

*Primary Examiner* — Jacob Cheu
(74) *Attorney, Agent, or Firm* — Pearl Cohen Zedek Latzer, LLP; Mark S. Cohen

(57) ABSTRACT

The present invention relates to methods for determining a risk or identifying a condition associated with the presence of endometriosis in a subject as well as testing a candidate compound for a therapeutic activity for the treatment of endometriosis and sorting patients based on the risk of having endometriosis. Specifically, the methods utilize novel markers for assessing the risk of the patient having endometriosis.

6 Claims, 6 Drawing Sheets

ENDOMETRIOSIS MARKERS

CROSS-REFERENCE TO RELATED APPLICATIONS

This application claims priority from U.S. patent application Ser. No. 11/314,098, filed Dec. 22, 2005, which claims priority U.S. Provisional Application Ser. No. 60/637,774, filed Dec. 22, 2004, both which are incorporated herein by reference in their entirety.

FIELD OF THE INVENTION

The present invention relates to methods for determining a risk or identifying a condition associated with endometriosis in a subject as well as testing a candidate compound for a therapeutic activity against endometriosis and sorting patients based on the risk of having endometriosis. Specifically, the methods utilize novel markers for assessing the risk of the patient having or developing endometriosis.

BACKGROUND OF THE INVENTION

Endometriosis is defined as the ectopic presence of endometrial glands and stroma. Endometriotic tissue is comprised of tissue that is histologically similar yet biochemically and functionally different or is out of phase from that of the uterine endometrium. The disease is estimated to affect 2-18% of reproductive age women and upwards of 40% of women with infertility. The ectopic endometrial tissues, which are predominantly found in dependent portions of the pelvis and on the ovaries, are hormonally active and result in hemorrhagic lesions, endometriomas, fibrosis and adhesion formation. Likewise, the peritoneal inflammation and the altered immune system response that is associated with endometriosis have been implicated in infertility by altering the processes of normal folliculogenesis, ovulation, fertilization, and implantation. Thus, endometriosis often results in multiple gynecological problems, including pelvic pain, dysmenorrhea, dyspareunia, and infertility.

The most commonly accepted theories regarding the pathophysiology of endometriosis purport that it arises from retrograde menstruation leading to adhesion of endometrial tissues to the surfaces of the pelvis and lower abdomen, or coelomic metaplasia of embryonic cells at rest found in the peritoneum and lining the Müllerian ducts. Recent studies have also presented evidence that alterations in an individual's humoral or cell-mediated immunity might make some women more susceptible to developing endometriosis.

At present, the definitive diagnosis of endometriosis requires surgery because imaging techniques, such as ultrasound and MRI, have not been shown to be reliable in the diagnosis or staging of the disease. In an effort to find a less invasive method to diagnose endometriosis, and based on the fact that endometriosis induces a local, and likely also a systemic, inflammatory process, numerous studies have focused on markers of inflammation in the peritoneal fluid and/or serum of women with the disease.

Over the past two decades, there has been much research in the molecular biology of endometriosis. Yet, despite a growing number of studies devoted to the disease, no one has been successful in developing a serum-based diagnostic test for endometriosis.

Therefore, a diagnostic test using specific endometriosis-related markers could be useful in diagnosis and nonsurgical management of the disease

SUMMARY OF THE INVENTION

In one embodiment, provided herein is a method of diagnosing or predicting the existence of endometriosis in a subject, comprising the steps of: determining an amount of macrophage chemoattractant protein-1 (MCP-1), macrophage migration inhibitory factor (MIF), Leptin, and Carcinoma Antigen-125 (CA-125) in a biological sample of the subject; and comparing the amount of said macrophage chemoattractant protein-1 (MCP-1), macrophage migration inhibitory factor (MIF), Leptin, and Carcinoma Antigen-125 (CA-125) to a reference standard, whereby if the amount determined for Carcinoma Antigen-125 (CA-125) and macrophage chemoattractant protein-1 (MCP-1) falls above the cutoff concentration defined by the reference standard for said Carcinoma Antigen-125 (CA-125) and macrophage chemoattractant protein-1 (MCP-1) marker, then the subject is at a high risk of having endometriosis.

In another embodiment, provided herein is a method of screening for a candidate compound having a therapeutic activity for treating endometriosis, comprising the steps of: analyzing the concentration of macrophage chemoattractant protein-1 (MCP-1), macrophage migration inhibitory factor (MIF), Leptin, and Carcinoma Antigen-125 (CA-125) in a biological sample of the subject; contacting said subject with said candidate compound; and re-analyzing the concentration of macrophage chemoattractant protein-1 (MCP-1), macrophage migration inhibitory factor (MIF), Leptin, and Carcinoma Antigen-125 (CA-125) in a biological sample of the subject whereby a decrease in the concentration of macrophage chemoattractant protein-1 (MCP-1), macrophage migration inhibitory factor (MIF), leptin, and Carcinoma Antigen-125 (CA-125) in the biological sample of the subject to below a cutoff concentration for each of macrophage chemoattractant protein-1 (MCP-1), macrophage migration inhibitory factor (MIF), leptin, and Carcinoma Antigen-125 (CA-125), indicates that the compound has therapeutic activity for treating endometriosis.

In one embodiment, provided herein is a method for sorting a subject based on the subject being at risk of having endometriosis, comprising the steps of: obtaining a serum sample from the subject; analyzing the subject's serum sample for the amount of macrophage chemoattractant protein-1 (MCP-1), macrophage migration inhibitory factor (MIF), Leptin, and Carcinoma Antigen-125 (CA-125); comparing the amount of macrophage chemoattractant protein-1 (MCP-1), macrophage migration inhibitory factor (MIF), Leptin, and Carcinoma Antigen-125 (CA-125) to a standard corresponding specifically to said macrophage chemoattractant protein-1 (MCP-1), macrophage migration inhibitory factor (MIF), Leptin, and Carcinoma Antigen-125 (CA-125) markers; and sorting the subjects based on the amount of the macrophage chemoattractant protein-1 (MCP-1), macrophage migration inhibitory factor (MIF), Leptin, and Carcinoma Antigen-125 (CA-125) markers relative to the range defined by the standards specific for the markers, whereby if the concentration of CA-125, MCP-1 MIF and Leptin are more than about 20.0 mIU/ml, 76.4 pg/ml, 14.7 ng/ml and 29.1 ng/ml respectively, the subject has endometriosis.

DETAILED DESCRIPTION OF THE INVENTION

Figure 1:
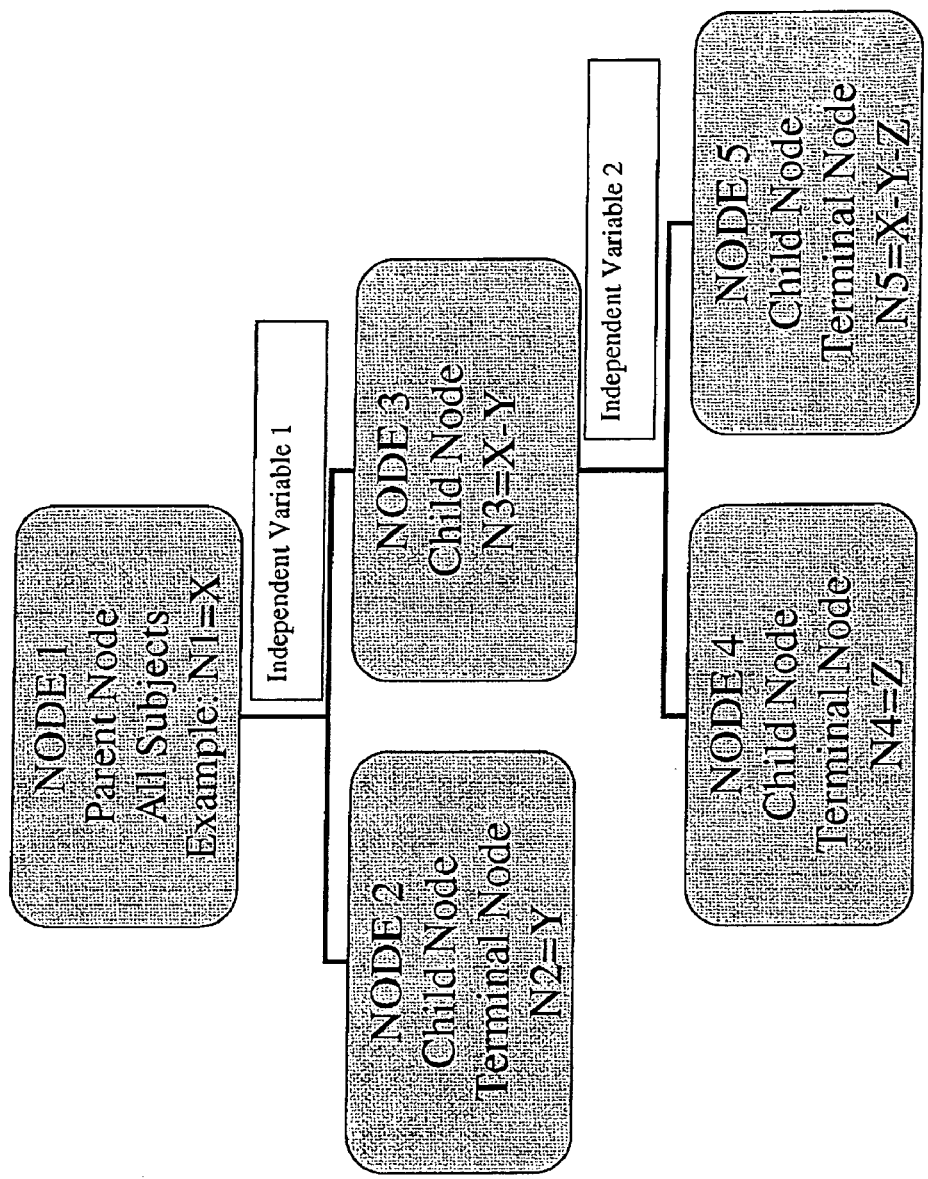
FIG. 1 shows a sample CART output with independent variables classifying subjects into binary groups.

In one embodiment, provided herein are methods for determining a risk or identifying a condition associated with endometriosis in a subject as well as testing a candidate compound for a therapeutic activity for treating endometriosis and sorting patients based on the risk of having endometriosis, without the need of invasive procedures.

In one embodiment, a panel of cytokines combined with Carcinoma Antigen-125 (CA-125) is useful for identifying a sub-group of patients who can be diagnosed based on combinations of these markers alone. In another embodiment, using the methods described herein, nearly one-half of patients would not need surgical diagnosis. The remainder may still require the traditional invasive diagnostic procedure. By following the methods described herein, a patient would be given the diagnosis of "endometriosis," "endometriosis-free," or "equivocal—further testing needed"

According to this aspect of the invention and in one embodiment, provided herein is a method of diagnosing or predicting the existence of endometriosis in a subject, comprising the steps of: determining an amount of macrophage chemoattractant protein-1 (MCP-1), macrophage migration inhibitory factor (MIF), Leptin, and CA-125 in a biological sample of the subject; and comparing the amount of said macrophage chemoattractant protein-1 (MCP-1), macrophage migration inhibitory factor (MIF), Leptin, and CA-125 to a reference standard, whereby if the amount determined for CA-125 and macrophage chemoattractant protein-1 (MCP-1) falls above the cutoff concentration defined by the reference standard for said CA-125 and macrophage chemoattractant protein-1 (MCP-1) marker, then the subject is at a high risk of having endometriosis.

The biological sample to be collected may consist in one embodiment of, or comprise blood, sera, urine, mucosa, sputum, epidermal sample, PAP smear, amniotic fluid, cultured cells, bone marrow sample or chorionic villi, and the like.

MCP-1 is a member of the C-C chemokine family and possesseschemotaxic activity for monocytes and T lymphocytes. MCP-1 is produced by stromal cells such as fibroblasts, endothelial cells, and monocytes and activates monocyte cytostatic function against tumor cells. Macrophage migration inhibitory factor (MIF) is released by monocytes and corticotropic anterior pituitary cells in response to, inter-alia, bacterial products, TNF-$\alpha$, interferon (IFN)-$\gamma$ and corticotropin releasing hormones (CRH). MIF exerts its biological function to inhibit the migration of macrophages, and stimulates TNF-$\alpha$ and nitric oxide from macrophages as well as IL-2 production. Leptin is a hormone that plays important roles in nutritional status and in obesity. Two populations of leptin-secreting cells were found in the lower half of the gastric mucosa. One consists of numerous large cells located around the gastric pits, the Chief epithelial cells, an the second in much smaller cells, few in number, and scattered between the gastric pits, the endocrine cells. In patients with advanced ovarian cancer the inflammatory response was found to be inversely related to leptin levels. Carcinoma Antigen-125 (CA-125) is expressed by most common epithelial ovarian carcinomas. In non-malignant tissue the antigen is frequently expressed in benign ovarian tumours of mucinous and non-mucinous origin as well as endometriosis. Different epitopes of the antigen may be expressed in the various conditions with increased tissue expression of the antigen.

In one embodiment, the step of determining the amount of said macrophage chemoattractant protein-1 (MCP-1), macrophage migration inhibitory factor (MIF), Leptin, and CA-125 comprises an immunological assay such as ELISA in one embodiment, a surface-enhanced laser desorption/ionization (SELDI) assay, a mass spectrometry, HPLC, or a combination thereof in other embodiments.

Each diagnostic method of the present invention can be used in the above method of testing a candidate compound for a therapeutic activity against endometriosis, and each diagnostic method represents a separate embodiment of the present invention.

According to this aspect of the invention and in one embodiment, provided herein is a a method of screening for a candidate compound having a therapeutic activity for treating endometriosis, comprising the steps of: analyzing the concentration of macrophage chemoattractant protein-1 (MCP-1), macrophage migration inhibitory factor (MIF), Leptin, and Carcinoma Antigen-125 (CA-125) in a biological sample of the subject; contacting said subject with said candidate compound; and re-analyzing the concentration of macrophage chemoattractant protein-1 (MCP-1), macrophage migration inhibitory factor (MIF), Leptin, and Carcinoma Antigen-125 (CA-125) in a biological sample of the subject whereby a decrease in the concentration of macrophage chemoattractant protein-1 (MCP-1), macrophage migration inhibitory factor (MIF), Leptin, and Carcinoma Antigen-125 (CA-125) in the biological sample of the subject to below a cutoff concentration for each of macrophage chemoattractant protein-1 (MCP-1), macrophage migration inhibitory factor (MIF), Leptin, and Carcinoma Antigen-125 (CA-125), indicates that the compound has therapeutic activity for treating endometriosis.

"Treating" or "treatment" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. Accordingly, provided herein is a composition for the treatment of endometriosis comprising the compound identified by the method of screening for a candidate compound having a therapeutic activity for treating endometriosis.

In another embodiment, the present invention provides a method of testing a candidate compound for a therapeutic activity against endometriosis, comprising (a) diagnosing a clinical state of a first female subject by a diagnostic method of the present invention, wherein the first female subject has not been contacted with the candidate compound; (b) diagnosing a clinical state of a second female subject by the a diagnostic method of the present invention, wherein the second female subject has not been contacted with the candidate compound; and (c) comparing the clinical state of a first female subject to the clinical state of a second female subject, whereby a decreased incidence of endometriosis in the first female subject relative to the second female subject indicates that the candidate compound has a therapeutic activity against endometriosis.

In one embodiment, endometriosis is classified into four stages (Stage I (Minimal), Stage II (Mild), Stage III (Moderate), & Stage IV (Severe)) of disease severity. The purpose of a classification system is to identify the relative severity of the disease process. The system is based upon the size, location, depth of invasion of endometrial implants and the amount of scar tissue involving the ovaries and fallopian tubes. Implants are further classified as red, white and black; while the red lesion category includes red, red-pink and clear lesions. Likewise, the white lesions includes white, peritoneal defect and yellow-brown lesions and the black lesion category includes both black and blue lesions. In one embodiment, the serum concentration of the markers provided herein will vary in accordance with the stage of the disease and may be used to diagnose the stage of disease by providing the level of the markers at each stage with its own cutoff concentration level.

Each diagnostic method of the present invention can be used in the above method of testing a candidate compound for a therapeutic activity against endometriosis, and each diagnostic method represents a separate embodiment of the present invention.

Misclassification bias may be eliminated in certain embodiments of the methods provided herein, by including in the disease group only those patients who had at least Stage II endometriosis found during surgery, thus excluding subjects with non-definitive findings. In another embodiment the control group may be heterogeneous with subjects who had other pathologies, including pain and infertility. This lends further supports the diagnostic algorithm provided in the methods described herein is specific to the disease process of endometriosis and not just an identifier of non-specific pain, infertility, or inflammation.

In another embodiment, the present invention provides a method of testing a candidate endometriosis marker, comprising (a) determining an amount of the candidate endometriosis marker in a biological sample from a female subject at risk of having endometriosis; (b) obtaining endometriosis status of the female subject (c) repeating steps (a)-(b) for a population of female subjects at risk of having endometriosis; and (d) ascertaining whether a correlation exists between the amount of the candidate marker and the endometriosis status, wherein a presence of the correlation indicates that the candidate endometriosis marker is useful in diagnosing endometriosis.

In another embodiment, ascertaining whether a correlation exists between the amount of the candidate marker and the endometriosis status utilizes a classification and regression tree analysis. CART analysis was used in Examples of the present invention to identify markers that correlate with endometriosis diagnoses, and can be similarly used for any other indicator of the status of a subject. Use of CART analysis is well known in the art, and is described, for example, in Vlahou A et al, J Biomed Biotechnol. 2003; 2003(5):308-314, incorporated herein by reference.

Using Classification and Regression Tree software, it was possible to re-examine the usefulness of serum levels of the most promising cytokines with CA-125 when used in combination as a multi-marker test. In one embodiment, using a panel of markers as described herein, is a more powerful system than examining the diagnostic properties of single cytokines and should therefore be adopted by persons holding ordinary skill in the art in the future. Assays for cytokines provided herein, such as MCP-1, and MIF in certain embodiments and CA-125 are commercially available to laboratories and can be thus easily ordered by clinicians who can then apply the diagnostic algorithms described in the methods provided herein. Although not all patients will be able to be diagnosed by these markers alone, a substantial number can be told their disease status with high accuracy and can thereby avoid diagnostic surgery.

In another embodiment, the ascertaining whether a correlation exists between the amount of the candidate marker and the endometriosis status is performed by any other statistical method known in the art. Each statistical method represents a separate embodiment of the present invention.

In another embodiment, the present invention provides a method of testing a candidate endometriosis marker, comprising (a) determining an amount of the candidate endometriosis marker in a biological sample from a female subject at risk of having endometriosis; (b) obtaining a clinical factor of the female subject, wherein the clinical factor is selected from: a maternal age, a gestational age, a clinical history, and a serum CA-125 level; (c) obtaining endometriosis status of the female subject; (d) repeating steps (a)-(c) for a population of female subjects at risk of having endometriosis; and (e) ascertaining whether a correlation exists between (i) a mathematical function of the concentration and the clinical factor; and (ii) the endometriosis stage, wherein a presence of the correlation indicates that the candidate endometriosis marker is useful in diagnosing endometriosis.

In one embodiment, the present invention provides a a method for sorting a subject based on the subject being at risk of having endometriosis, comprising the steps of: obtaining a serum sample from the subject; analyzing the subject's serum sample for the amount of macrophage chemoattractant protein-1 (MCP-1), macrophage migration inhibitory factor (MIF), Leptin, and Carcinoma Antigen-125 (CA-125); comparing the amount of macrophace chemoattractant protein-1 (MCP-1), macrophage migration inhibitory factor (MIF), Leptin, and Carcinoma Antigen-125 (CA-125) to a standard corresponding specifically to said macrophage chemoattractant protein-1 (MCP-1), macrophage migration inhibitory factor (MIF), Leptin, and Carcinoma Antigen-125 (CA-125) markers; and sorting the subjects based on the amount of the macrophage chemoattractant protein-1 (MCP-1), macrophage migration inhibitory factor (MIF), Leptin, and Carcinoma Antigen-125 (CA-125) markers relative to the range defined by the standards specific for the markers, whereby if the concentration of CA-125, MCP-1 MIF and Leptin are more than about 20.0 mIU/ml, 76.4 pg/ml, 14.7 ng/ml and 29.1 ng/ml respectively, the subject has endometriosis.

Immunological or other assays will then be developed for detection of each of these markers, further improving the assays of the present invention. In one embodiment the marker Leptin may be replaced by another marker having substantial homology to leptin.

Methods of protein sequencing are well known in the art, and are described, for example, in Lodish et al, Molecular Cell Biology, Fourth Edition, W. H. Freeman, 2000; and Berg et al, Biochemistry, Fifth Edition, 2002). Each protein sequencing method represents a separate embodiment of the present invention.

The term "about" refers in one embodiment to quantitative terms plus or minus 5%, or in another embodiment plus or minus 10%, or in another embodiment plus or minus 15%, or in another embodiment plus or minus 20%.

The terms "homology," "homologous," etc., when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined in the latter case by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, homology is determined is via determination of candidate sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, New York; and Ausubel et al., 1989, Current Protocols in Molecular Biology, Green Publishing Associates and Wiley Interscience, New York). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In one embodiment, the method of determining the amount of one or more of the proteins or peptides of the present invention comprises an immunological assay. In one embodiment, the immunological assay is a radio-immunoassay (RIA). In another embodiment, the immunological assay is an enzyme-linked immunosorbent assay (ELISA). In another embodiment, the immunological assay is a sandwich immunoassay. In another embodiment, the immunological assay is any other immunological assay known in the art. Each immunological assay represents a separate embodiment of the present invention.

Methods of performing immunological assays are well known in the art, and are described, for example, in *Current Protocols in Immunology*, John Wiley & Sons, 2004. Each immunological assay represents a separate embodiment of the present invention.

In another embodiment, the method of determining the amount of one or more of the proteins or peptides of the present invention comprises a surface-enhanced laser desorption/ionization (SELDI) assay.

In one embodiment, the SELDI utilizes a weak cation exchange (WCX2) chemistry. In another embodiment, the SELDI utilizes Immobilized Metal Affinity Capture (IMAC) chemistry. In one embodiment, the IMAC chemistry comprises a copper ion. In another embodiment, the chemistry is similar to WCX2 chemistry (e.g. an improved or altered version thereof). In another embodiment, the chemistry is similar to IMAC chemistry. Each possibility represents a separate embodiment of the present invention.

The term "subject" refers in one embodiment to a mammal including a human in need of therapy for, or susceptible to, a condition or its sequalae. The subject may include dogs, cats, pigs, cows, sheep, goats, horses, rats, and mice and humans. The term "subject" does not exclude an individual that is normal in all respects. In one embodiment, the term "subject" for purposes of diagnosis, or risk factors assessment refers to a human subject who is pregnant. The subject, in one embodiment is at risk of or exhibiting symptoms associated with endometriosis due to having high serum concentrations of chemoattractant protein-1 (MCP-1), macrophage migration inhibitory factor (MIF), Leptin, and CA-125, and the like.

In one embodiment, determination of the marker protein or peptide used in embodiments of methods described herein is done by using an immunological assay, a surface-enhanced laser desorption/ionization (SELDI) assay, a mass spectrometry, or a combination thereof.

The following examples are presented in order to more fully illustrate the preferred embodiments of the invention. They should in no way be construed, however, as limiting the broad scope of the invention.

EXAMPLES

Materials and Methods

General Protocol

This study was approved by the Institutional Review Board of the University of Pennsylvania. Serum was obtained from women of reproductive age (18-50 years old) already scheduled for laparoscopic surgery (for whom the gold standard diagnosis would be known). Enrollment took place between December 2003 and November 2005. The subjects underwent surgery for the indications of infertility, pelvic pain, tubal sterilization or tubal reversal, or other benign etiology. Written informed consent for the collection of clinical information and peripheral blood was obtained prior to surgery. Blood was collected via peripheral draw in serum-separator tubes, samples were centrifuged at 13,200 rpm for 10 minutes, and the serum was aliquoted and stored at −70° C. until analysis. During the laparoscopy, evidence of endometriosis was recorded and staged, according to the published revised ASRM scoring system. Subjects were allocated to groups based on their post-surgical diagnosis. To avoid the error of misclassification bias, only those subjects who had at least stage II endometriosis diagnosed during surgery were included in the diseased group. Women with stage I disease were excluded and considered neither a case nor a control.

Laboratory Methods

Serum concentrations of seven markers (IL-6, TNF-α, MIF, MCP-1, IFN-γ, Leptin, and CA-125) were evaluated using commercially available Enzyme-Linked Immunosorbent Assay (ELISA) kits (R&D Systems, Inc., Minneapolis, Min., USA and Panomics, Inc., Redwood City, Calif., USA for CA-125). The optical density (OD) was measured at 450 nm with λ correction at 650 nm. Cytokine and CA-125 levels were extrapolated from standard curves of known concentrations. All samples in the ELISA assays were run in duplicate.

The sensitivities of the IL-6, TNF-α, MIF, MCP-1, IFN-Ξ, Leptin, and CA-125 ELISAs were 0.70, 1.6, 0.017, 5.0, 8.0, 780 pg/mL and 5 U/mL, respectively, with standard curve ranges of 3.12-300, 1.9-125, 1.5-100, 15.6-1000, 7.8-500, 780-100,000 pg/mL and 7.5-400 U/mL, respectively.

Statistical Analyses

Sensitivity and specificity for each proposed marker were assessed with receiver operating characteristic (ROC) curves [28]. The area under the ROC curve was calculated as a measure of the ability of each potential marker to discriminate between endometriosis cases and non-cases (controls). An area under the curve of 0.5 indicates classifications assigned by chance. Mean concentrations of the markers, and the differences in means between groups, were purposely not computed as these would not be of clinical usefulness and could not be used for diagnostic purposes.

The diagnostic performance of the markers was then evaluated jointly using classification tree analysis (CART, Sanford Systems). Classification and Regression Tree (CART) is a nonparametric statistical procedure that examines all possible dichotomous splits on each marker and selects the variable and cut-off value that results in a grouping which best classifies the subjects with respect to the dependent variable (endometriosis or control) [FIG. 1]. In this way, two child nodes are created from each parent note. The tree-growing methodology continues by assessing each of the remaining markers to determine which variable and cut-off value results in the next best split for each of the child nodes. This algorithm continues until terminal nodes are reached, which are defined as mutually exclusive and exhaustive subgroups of the study population. Although the CART method can continue until each subject is accurately classified, this often yields a tree with so many branches that it would be unwieldy and not clinically useful. Thus, one needs to prune back the tree and choose a tree that has good diagnostic properties, yet is parsimonious.

Bootstrapping was carried out as part of the tree-building methodology as a form of internal validation. By randomly altering the weights that cases had in the analysis, this method re-sampled the data with replacement and allowed for testing the stability of the trees.

Example 1

Panel of 4 Cytokines used Together, but not Alone, Accurately Predict Endometriosis Specific Marker Analysis A total of 197 patients were enrolled in the study. Sixty-three (63) patients had Stage II through IV endometriosis and were assigned to the disease group; 78 were endometriosis-free and were assigned to the control group. The remaining 56 women were diagnosed with Stage I endometriosis and were excluded from the analyses because of concern of equivocal diagnosis. The demographic and clinical data of the subjects in the two groups are presented in Table 1.

|  | Endometriosis (N = 63) | Control (N = 78) | p |
|---|---|---|---|
| Mean age in years (Range) | 34 (18-48) | 33 (23-48) | 0.28 |
| Race (%): |  |  |  |
| Caucasian | 53 (84%) | 39 (50%) | <0.001 |
| African Am. | 4 (6%) | 36 (46%) | <0.001 |
| Hispanic | 1 (2%) | 2 (3%) | 0.69 |
| Asian | 5 (8%) | 1 (1%) | .05 |
| Endometriosis (%): |  |  |  |
| Stage II | 22 (35%) | N/A |  |
| Stage III | 17 (27%) | N/A |  |
| Stage IV | 24 (38%) | N/A |  |
| Indication for Surgery (%) |  |  |  |
| Pain | 40 (64%) | 21 (27%) | <0.001 |
| Infertility | 22 (35%) | 25 (32%) | 0.72 |
| BTL | 0 | 27 (35%) | <0.001 |
| Other benign | 1 (1%) | 5 (6%) | 0.16 |
| Reported Pelvic Pain (%) | 51 (81%) | 29 (37%) | <0.001 |
| Reported Pain Severity (%) |  |  |  |
| Mild | 4 (6%) | 5 (6%) | 0.99 |
| Moderate | 25 (40%) | 11 (14%) | 0.001 |
| Severe | 20 (32%) | 12 (15%) | 0.02 |
| Missing | 2 (3%) | 1 (5%) | 0.43 |
| Reported Dyspareunia (%) | 22 (35%) | 13 (17%) | 0.01 |
| Current OCP use (%) | 17 (27%) | 14 (18%) | 0.20 |

Figure 2:
FIG. 2 shows marker concentrations by study groups showing the overlap in concentrations of the individual markers among the endometriosis and the control groups.

The concentrations in serum of the 6 cytokines and CA-125 were evaluated singly via ROC analysis to identify differential cut-points that would predict disease status. The levels of IFN-gamma were below the assay's limit for detection for almost all subjects tested and were thus excluded from the analyses. There was a great deal of overlap in the concentrations of the remaining 6 markers between the two study groups, as shown graphically in FIG. 2.

Figure 3:
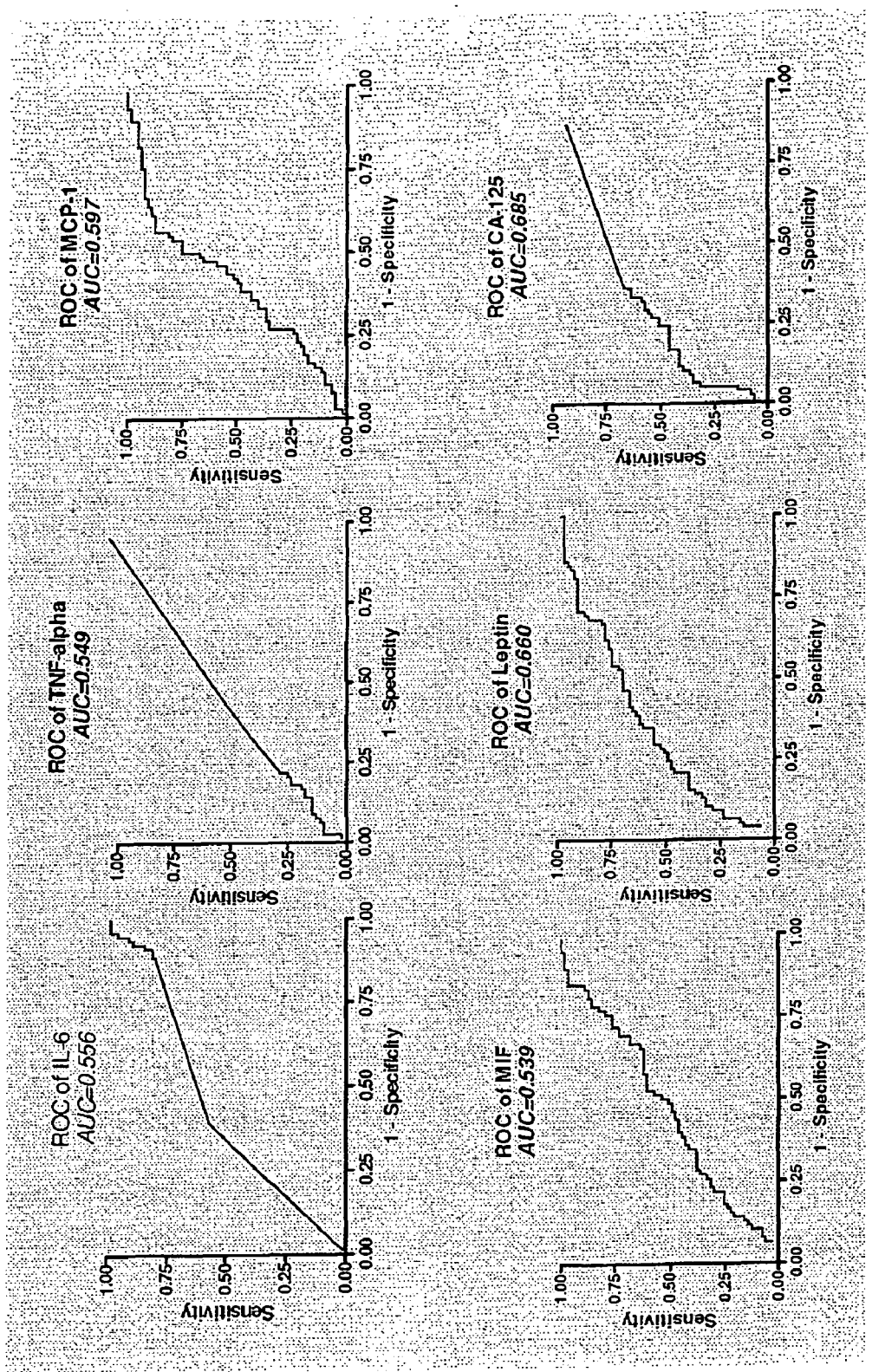
FIG. 3 shows receiver operator characteristic (ROC) curves and area under the curve (AUC) with 95% Confidence Intervals for each marker: IL-6=0.556 (0.454-0.650); TNF-alpha=0.549 (0.453-0.645); MCP-1=0.597 (0.503-0.691); MIF=0.539 (0.443-0.634); Leptin=0.660 (0.569-0.751); CA-125=0.685 (0.595-0.774)

Receiver-operator curves for each marker confirmed the overall poor performance of the markers taken one at a time. Among the markers, CA-125 performed the best, with an area under the curve (AUC) of 0.685 (95% CI 0.595-0.774). Since the confidence interval did not cross 0.5, we can be reasonably certain that CA-125 performed significantly better than chance alone. The ROC curves with AUC and confidence intervals for each marker are shown in FIG. 3.

CART Analysis

Figure 4:
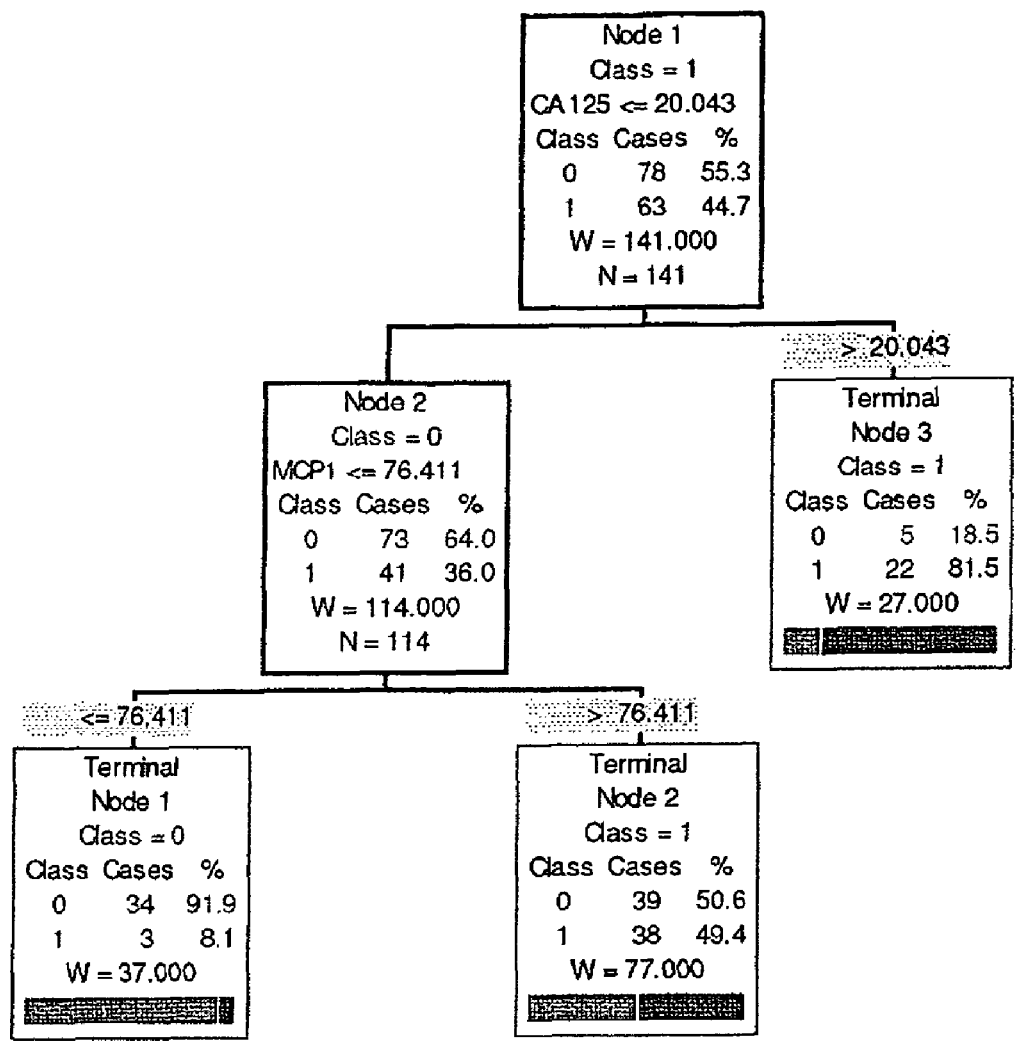
FIG. 4 shows marker Classification Tree Optimizing Sensitivity. The Class assignment of subjects in each node is shown under the node number. Class 0 is the control group and Class 1 is the Endometriosis group. Bars give a graphical representation of the proportion of subjects from each group assigned to that child node. Splitting variables are shown in the parent node, with the cut-off for the split shown above the child node in grey. N=number of subjects
Figure 5:
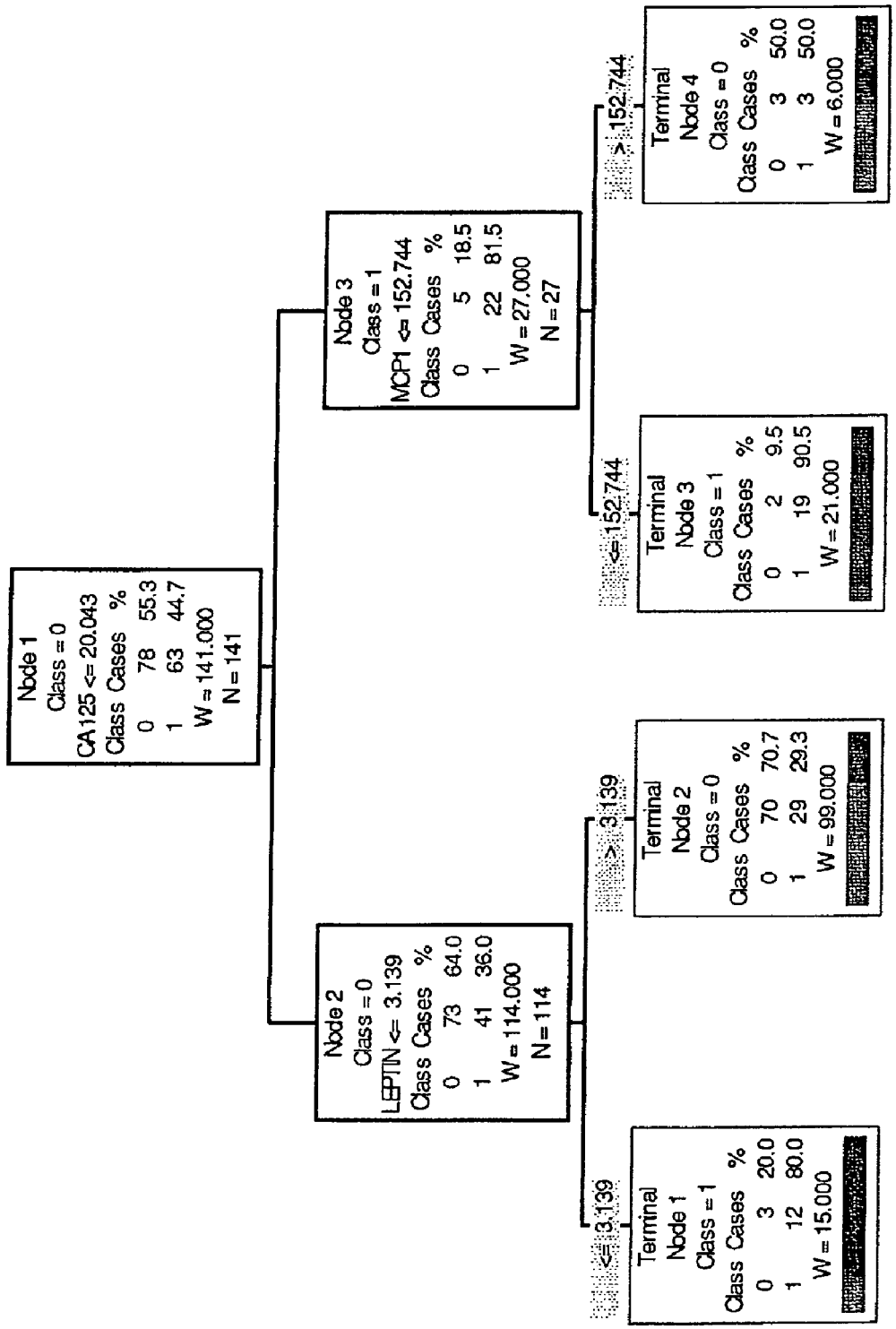
FIG. 5 shows Marker Classification Tree Optimizing Specificity.

CART analysis of the six markers jointly found that the best combination with the fewest variables that differentiated the diseased from the control subjects was CA-125, MCP-1, and Leptin. Using those three markers, a two-step diagnostic algorithm was followed which used information from two classification trees. The first tree used a cut-off of >20.0 mIU/mL for CA-125 and >76.4 pg/mL for MCP-1 to classify those who have endometriosis (FIG. 4). Together, these markers bad a sensitivity of 95% (95% CI: 87, 99%) and specificity of 44% (95% Cl: 32, 55%). The second tree was defined by CA-125 with a cut-off of ≦20.0 mIU/mL, Leptin at a cut-off of ≦3.14 ng/mL and MCP-1 at a cut-off of ≦152.7 pg/mL to classify those without endometriosis (FIG. 5). This three-marker tree maximized specificity at 94% (95% CI: 86, 98%) with a sensitivity of 49% (95% CI: 36, 62%). Bootstrapping did not alter these outputs.

Only subjects who were classified as having endometriosis (or being disease-free) consistently by the two trees were assigned that classification. In other words, subjects who were classified as 'Endometriosis' on both trees were assigned the disease diagnosis, those who were classified as 'No Endometriosis' were assigned the no disease diagnosis, and those whose classifications did not match remained unassigned. The two-tiered algorithm described above had a combined accuracy of 89% with 3 false negatives and 5 false positives. A total of 45% (64/141) subjects received a diagnosis.

Figure 6:
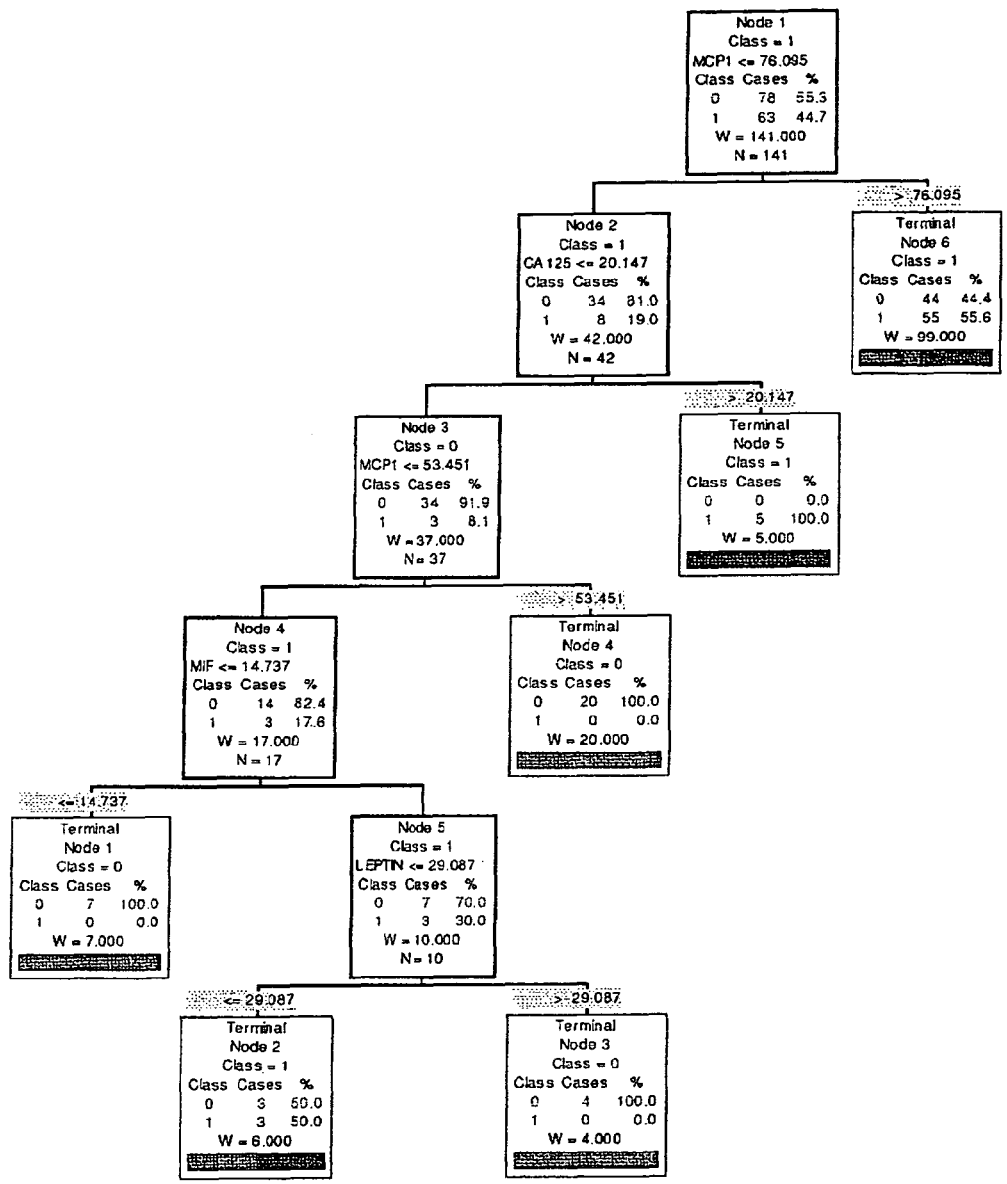
FIG. 6 shows Marker Classification Tree with 100% Sensitivity

Alternatively, adding two additional markers to a tree that included CA-125 and MCP-1, MIF at a cut-point of >14.7 ng/mL and Leptin at a cut-point of >29.1 ng/mL, improved sensitivity to 100% (95% CI: 94, 100%) with a specificity of 40% (95% CI: 29, 51%) as shown in FIG. 6. Again, these trees remained stable after bootstrapping. Changing the diagnostic algorithm to include this tree in parallel with the tree that maximized specificity (FIG. 5) eliminated the error of false-negative diagnosis. This algorithm could diagnose 31/63 (49%) subjects with endometriosis with 100% (31/31) accuracy and an additional, 36/78 (46%) subjects without endometriosis as disease-free. In this situation there were 5 false positives resulting in 86% (31/36) accuracy. Overall, 67/141 subjects (48%) received a diagnosis with the marker panel alone. The overall accuracy of diagnosis was 93% (62/67). The remaining 74 subjects could not be diagnosed by the panel of markers and would have had to undergo standard diagnostic methods.

A summary of the diagnostic performance of the two sets of markers and algorithms is presented in Table 2.

TABLE 2

Comparison of Diagnostic Performance using Markers

| Diagnostic Algorithm | # Diagnosed by test (total) | # Subjects w/Endo diagnosed | # Subjects w/o Endo diagnosed | # False Positives | # False Negatives | Combined Accuracy |
|---|---|---|---|---|---|---|
| 3 Markers: CA-125, MCP-1 & Leptin | 72/141 (51%) | 33/63 (52%) | 39/78 (50%) | 5/39 | 3/33 | 64/72 (89%) |
| 4 Markers: CA-125, MCP-1, Leptin & MIF | 67/141 (48%) | 31/63 (49%) | 36/78 (46%) | 5/36 | 0/31 | 62/67 (93%) |

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of diagnosing or predicting the existence of endometriosis in a subject, comprising the steps of:
   a. determining an amount of macrophage chemoattractant protein-1 (MCP-1), and carcinoma antigen-125 (CA-125) in a biological sample of the subject; and
   b. comparing the amount of said MCP-1 and said CA-125 to a reference standard, whereby if the amount determined for said MCP-1 and said CA-125 falls above the cutoff concentration defined by the reference standard for said MCP-1 and said CA-125, then the subject is at a high risk of having endometriosis, wherein the cutoff concentration for said MCP-1 and said CA-125 is about 76.4 pg/ml and about 20.0 mIU/ml, respectively, and wherein the reference standard is derived from samples collected from a population that excludes stage I endometriosis.

2. The method of claim 1, whereby the step of determining the amount of said MCP-1 and said CA-125 comprises an immunological assay, a surface-enhanced laser desorption/ionization (SELDI) assay, a mass spectrometry, or a combination thereof.

3. The method of claim 1, whereby said biological sample is a serum sample.

4. The method of claim 1, whereby the step of determining further comprising determining an amount of macrophage migration inhibitory factor (MIF) and Leptin in said biological sample of the subject and the step of comparing further comprising comparing the amount of said (MIF) and said Leptin, to a reference standard, whereby if the amount determined for said MIF and said Leptin falls above the cutoff concentration defined by the reference standard for said MIF and said Leptin, then the subject is defined as having endometriosis.

5. The method of claim 4, whereby the cutoff concentration for said MIF and said Leptin is 14.7 ng/ml and 29.1 ng/ml respectively.

6. A method for sorting a subject based on the subject being at risk of having endometriosis, comprising the steps of:
   a. obtaining a serum sample from the subject;
   b. analyzing the subject's serum sample for the amount of macrophage chemoattractant protein-1 (MCP-1), macrophage migration inhibitory factor (MIF), Leptin, and carcinoma antigen-125 (CA-125;
   c. comparing the amount of said MCP-1, MIF, Leptin, and CA-125 to a standard corresponding specifically to said MCP-1, MIF, Leptin, and CA-125 markers; and
   d. sorting the subjects based on the amount of said MCP-1, MIF, Leptin, and CA-125 markers relative to the range defined by the standards specific for the markers, whereby if the concentration of CA-125, MCP-1 MIF and Leptin are more than about 20.0 mIU/ml, 76.4 pg/ml, 14.7 ng/ml and 29.1 ng/ml respectively, the subject has endometriosis,
   wherein the reference standard is derived from samples collected from a population that excludes stage I endometriosis.

* * * * *